US009808982B2

(12) United States Patent
Kleine et al.

(10) Patent No.: US 9,808,982 B2
(45) Date of Patent: Nov. 7, 2017

(54) TAPERED POLYMERIC STENT AND METHOD OF FABRICATING SAME

(71) Applicant: Abbott Cardiovascular Systems Inc., Santa Clara, CA (US)

(72) Inventors: Klaus Kleine, Los Gatos, CA (US); David C. Gale, Kennesaw, GA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 58 days.

(21) Appl. No.: 14/542,395

(22) Filed: Nov. 14, 2014

(65) Prior Publication Data

US 2016/0046058 A1   Feb. 18, 2016

Related U.S. Application Data

(62) Division of application No. 12/816,275, filed on Jun. 15, 2010, now abandoned, which is a division of
(Continued)

(51) Int. Cl.

| | |
|---|---|
| *B29C 49/00* | (2006.01) |
| *A61F 2/844* | (2013.01) |
| *A61F 2/915* | (2013.01) |
| *B29C 49/42* | (2006.01) |
| *A61F 2/91* | (2013.01) |
| *B29C 49/48* | (2006.01) |
| *B29C 49/54* | (2006.01) |
| *B29L 31/00* | (2006.01) |
| *B29K 67/00* | (2006.01) |

(52) U.S. Cl.
CPC .......... *B29C 49/0073* (2013.01); *A61F 2/844* (2013.01); *A61F 2/91* (2013.01); *A61F 2/915* (2013.01); *B29C 49/4278* (2013.01); *B29C 49/48* (2013.01); *A61F 2210/0004* (2013.01); *A61F 2230/0067* (2013.01); *A61F 2230/0069* (2013.01); *A61F 2240/001* (2013.01); *A61F 2250/0068* (2013.01); *B29C 49/54* (2013.01); *B29C 2049/0089* (2013.01); *B29C 2793/009* (2013.01); *B29K 2067/046* (2013.01); *B29K 2995/0056* (2013.01); *B29L 2031/7534* (2013.01)

(58) Field of Classification Search
CPC .. A61F 2/844; A61F 2/91; A61F 2/915; A61F 2210/0004; A61F 2230/0067; A61F 2230/0069; A61F 2240/001; A61F 2250/0068; B29C 2049/0089; B29C 49/0073; B29C 49/4278; B29C 2793/009; B29C 49/48; B29C 49/54; B29K 2067/046; B29K 2995/0056; B29L 2031/7534
See application file for complete search history.

(56) References Cited

U.S. PATENT DOCUMENTS

| | | | |
|---|---|---|---|
| 6,574,851 B1 * | 6/2003 | Mirizzi .................... | A61F 2/91 264/219 |
| 2006/0076708 A1 * | 4/2006 | Huang ..................... | A61F 2/91 264/239 |
| 2006/0229695 A1 * | 10/2006 | Brown ...................... | A61F 2/91 623/1.3 |

\* cited by examiner

*Primary Examiner* — Robert J Grun
(74) *Attorney, Agent, or Firm* — Squire Patton Boggs (US) LLP

(57) ABSTRACT

A polymeric stent has an inner surface with an inner diameter that tapers continuously in size. A method for manufacturing a stent includes blow molding a polymeric tube within a mold having a tapered, cylindrical cavity such that the polymeric tube attains a corresponding tapered shape. The tapered tube is used as a substrate from which a laser cuts interconnecting stent struts.

18 Claims, 6 Drawing Sheets

Related U.S. Application Data application No. 11/479,111, filed on Jun. 30, 2006, now Pat. No. 7,740,791.

FIG. 6A
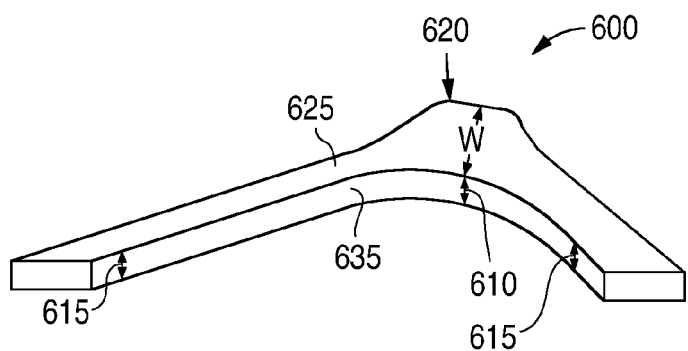
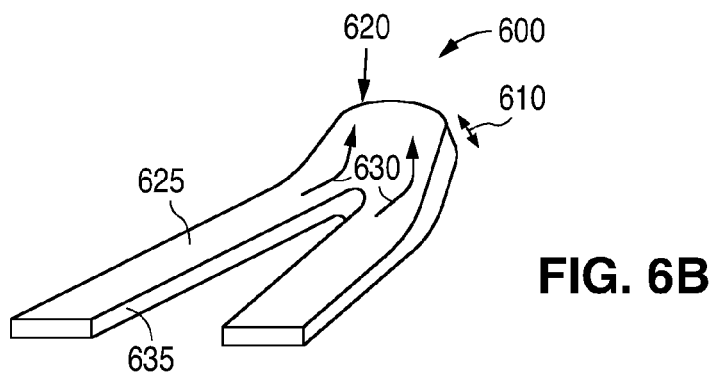
FIG. 6B
FIG. 7A
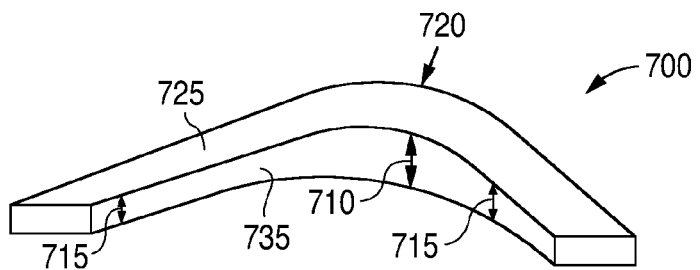
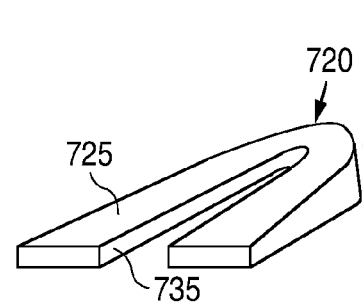
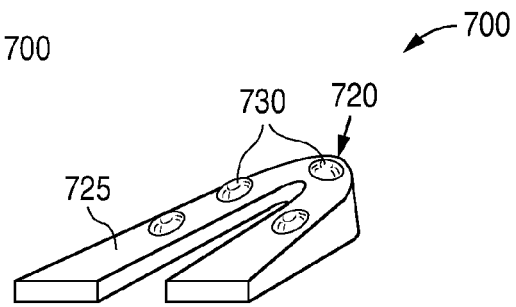
FIG. 7B    FIG. 7C

TAPERED POLYMERIC STENT AND METHOD OF FABRICATING SAME

CROSS-REFERENCE TO RELATED APPLICATION

This application is a divisional application Ser. No. 12/816,275, filed Jun. 15, 2010 which is a divisional of application Ser. No. 11/479,111, filed Jun. 30, 2006, now U.S. Pat. No. 7,740,791, the entire contents of both applications are hereby incorporated by reference.

FIELD OF THE INVENTION

This invention relates to a method of fabricating a stent.

BACKGROUND OF THE INVENTION

This invention relates to radially expandable endoprostheses which are adapted to be implanted in a body lumen. An "endoprosthesis" corresponds to an artificial implantable medical device that is placed inside the body. A "lumen" refers to a cavity of a tubular organ such as a blood vessel. These endoprostheses are commonly referred to as stents. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

The cylindrical structure of stents is typically composed of a scaffolding that includes a pattern or network of interconnecting structural elements or struts. The scaffolding can be formed from wires, tubes, or planar films of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and radial rigidity is needed to hold open a body lumen. The pattern should be designed to maintain the necessary longitudinal flexibility and radial rigidity of the stent.

A number of techniques have been suggested to fabricate stents from tubes and planar films or sheets. One such technique involves laser cutting or etching a pattern onto a material. Laser cutting may be performed on a planar film of a material which is then rolled into a tube. Alternatively, a desired pattern may be etched directly onto a tube. Fabricating a stent from a tube is preferable due to time and cost considerations. Other techniques involve cutting a desired pattern into a sheet or a tube via chemical etching or electrical discharge machining Laser cutting of stents has been described in a number of publications including U.S. Pat. No. 5,780,807 to Saunders, U.S. Pat. No. 5,922,005 to Richter and U.S. Pat. No. 5,906,759 to Richter.

It is desirable for a stent to have certain mechanical properties to facilitate delivery and deployment of a stent, especially in the bending portions of the stent that are bent during crimping and expansion of the stent. For example, longitudinal flexibility is important for successful delivery of the stent. In addition, radial rigidity and strength are vital characteristics in deployment and for holding open a body lumen. The pattern that makes up the stent allows the stent to be radially expandable and longitudinally flexible. The pattern should be designed to maintain the necessary longitudinal flexibility and radial rigidity of the stent. One technique for strengthening the bending portions of a stent is to laser cut the stent such as to widen the bending portions of the stent. However, upon crimping a stent that includes wider bending portions, oftentimes the stent flips upwards or "chip" when the strut is bent during crimping and/or expansion.

What is needed in the art is a method of fabricating a stent to mechanically strengthen the stent in selected portions.

SUMMARY OF THE INVENTION

Briefly and in general terms, the present invention is directed to a stent and a method of manufacturing a stent.

In aspects of the invention, a method comprises disposing a polymeric tube into a cylindrical mold, the cylindrical mold having a variable diameter along a portion of the inside surface of the mold; radially expanding the tube by blowing a gas or liquid into the cylindrical mold, the outside surface of the tube conforming to the variable diameter portion of the inside surface of the mold, causing the radially expanded tube to have a variable diameter along the conformed length of the tube; and fabricating a stent from the expanded tube.

In other aspects of the invention, a method comprises disposing a polymeric tube into a cylindrical mold, the cylindrical mold comprising an inner surface facing the polymeric tube, the inner surface having an inner diameter that varies along an axial length of the cylindrical mold. The method further comprises expanding the polymeric tube in radially outward directions to form an expanded tube, the expanding including blowing a gas or liquid into the cylindrical mold so that an outer surface of the polymeric tube conforms to the inner surface of the cylindrical mold and so that the outer surface of the expanded tube has an outer diameter that varies along an axial length of the expanded tube. The method further comprises fabricating a stent from the expanded tube.

In other aspects of the invention, a stent is formed from a polymeric tube that was disposed into a cylindrical mold, subsequently expanded in radially outward directions in the cylindrical mold, and subsequently removed from the cylindrical mold and cut to form interconnecting stent struts, wherein the polymeric tube has an outer surface with an outer diameter that, after being removed from the cylindrical mold, varies along an axial length of the polymeric tube.

BRIEF DESCRIPTION OF THE DRAWINGS

FIG. 6A depicts a portion of a strut having a uniform thickness and a relatively wider bending portion.

FIG. 6B depicts a portion of a strut after crimping, where portion of strut has a uniform thickness and the wider bending portion that has flipped upward.

FIG. 7A depicts a portion of a strut before crimping having a relatively thicker bending portion.

FIG. 7B depicts a portion of a strut after crimping having a relatively thicker bending portion.

FIG. 7C depicts a portion of a strut having a relatively thicker bending portion, and, in addition, features on the abluminal or luminal side.

DETAILED DESCRIPTION OF THE INVENTION

For the purposes of the present invention, the following terms and definitions apply:

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Elastic limit" refers to the maximum stress that a material will withstand without permanent deformation.

"Strength" refers to the maximum stress in a direction in testing which a material will withstand prior to fracture. The ultimate strength is calculated from the maximum load applied during the test divided by the original cross-sectional area.

"Strain" refers to the amount of elongation or compression that occurs in a material at a given stress or load. Elongation may be defined as the increase in length which occurs when subjected to stress. It is typically expressed as a percentage of the original length.

The "glass transition temperature," Tg, is the temperature at which the amorphous domains of a polymer change from a brittle vitreous state to a plastic state at atmospheric pressure. In other words, the Tg corresponds to the temperature where the onset of segmental motion in the chains of the polymer occurs. Tg of a given polymer can be dependent on the heating rate and can be influenced by the thermal history of the polymer. Above Tg, molecular orientation may be induced with applied stress since rotation of polymer chains, and hence segmental mobility is possible. Between Tg and the melting temperature of the polymer, $T_m$, rotational barriers exist, however, the barriers are not great enough to substantially prevent segmental mobility. As the temperature of a polymer is increased above Tg, the energy barriers to rotation decrease and segmental mobility of polymer chains tend to increase. As a result, as the temperature increases, molecular orientation is more easily induced with applied stress.

Figure 1:
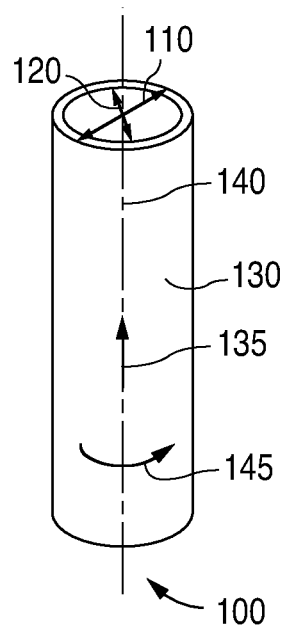
FIG. 1 depicts a tube for use in forming a stent.

Embodiments of the method can be used to fabricate devices including, but not limited to, stents, balloon-expandable stents, stent-grafts, and grafts. Various embodiments to manufacture a stent with desirable features are described herein. Some embodiments to manufacture the device include fabricating the stent from a polymer conduit or tube. The tube may be cylindrical or substantially cylindrical in shape. For example, FIG. 1 depicts a tube 100. Tube 100 is a cylinder with an outside diameter 110 and an inside diameter 120. FIG. 1 also depicts an outside surface 130 and a cylindrical axis 140 of tube 100. When referred to below, unless otherwise specified, the "diameter" of the tube refers to the outside diameter of tube.

Figure 2:
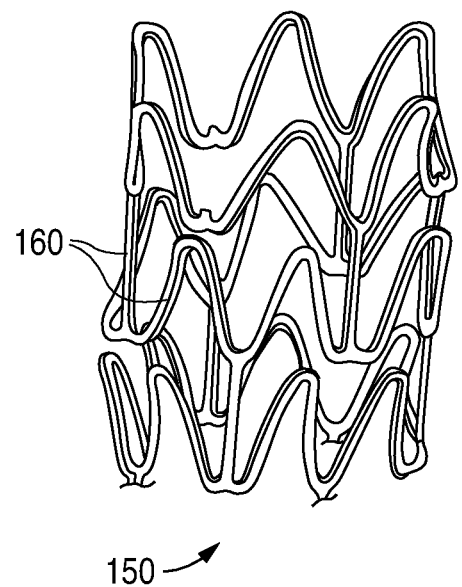
FIG. 2 depicts a three-dimensional stent with a pattern.

The polymeric tube may be used to fabricate a stent. Fabrication may include forming a pattern that includes at least one interconnecting element or strut on the elongated tube. The stent may be formed by laser cutting a pattern on the elongated tube. Representative examples of lasers that may be used include an ultra fast laser, excimer, carbon dioxide, and YAG. Chemical etching may also be used to form a pattern on the elongated tube. FIG. 2 depicts a three-dimensional view of a stent 150 which may be formed from tube 100 in FIG. 1. FIG. 2 depicts a pattern or network of struts 160. The pattern is not limited to the depicted stent pattern.

The polymeric tube for use in manufacturing a stent has a desired strength and flexibility in the longitudinal direction, as shown by an arrow 135 in FIG. 1, and in the transverse or radial direction, as shown by an arrow 145 in FIG. 1. The desired strength and flexibility can be induced by radial expansion and/or axial deformation. A tube can be radially deformed by blow molding. The invention provides blow molding a tube to form a tube having a variable diameter and/or features such as indentations. There are many advantages to fabricating tubes with a variable diameter and/or features such as indentions, such as increased stent retention and features such as pockets filled with drugs or radio-opaque substances.

Several embodiments disclosed herein provide applying radial pressure to a polymeric tube by positioning the polymeric tube within a cylindrical mold. The cylindrical mold may include features where, upon conveying a gas or liquid at a selected pressure into a proximal end of the polymeric tube, the cylindrical mold acts to control the diameter of the expanded polymeric tube by limiting the expansion to the inside diameter of the cylindrical mold. The pressure of the conveyed gas may be used to control the expansion of the polymeric tube to a desired diameter, while a distal end of the polymeric tube may be closed. The inside diameter of the cylindrical mold with features corresponds to the desired shape and diameter of the formed polymeric tube. The inside surface of the mold may include features such as protrusions, projections, grooves, indentations, flanges, overhangs, and extensions. Other features are also possible. The embodiments disclosed herein allow formation of a tube with a variable diameter and/or features on the outside surface of the tube. The invention also provides fabricating a stent having portions that are thicker than other portions of the stent.

Figure 3A:
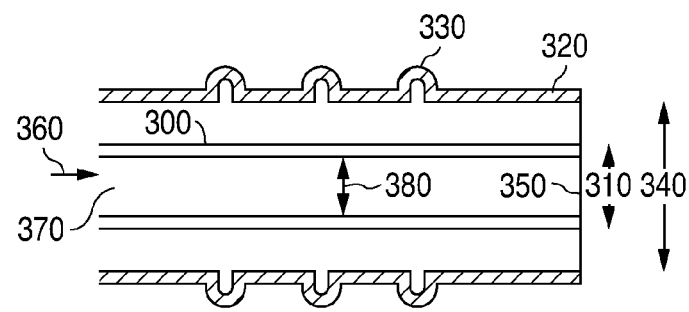
FIG. 3A depicts an axial cross-section of a polymeric tube inserted in a cylindrical mold having indentations.

FIG. 3A depicts an axial cross-section of a polymeric tube 300 with an outside diameter 310 positioned within a cylindrical mold 320 having indentations 330 on the inside surface of the mold 320. Cylindrical mold 320 with indentations 330 acts to limit the expansion of polymeric tube 300 to the inside surface of mold 320. The indentations form a tube 300 with a variable diameter. When the polymeric tube 300 expands from diameter 310 to diameter 340, protrusions 390 are formed on the outside surface of the polymeric tube 300.

Polymeric tube 300 may be closed at a distal end 350 to conform to the outside surface of mold 320. Any gas, such as air, may be conveyed, as indicated by an arrow 360, into an open proximal end 370 of polymeric tube 300. A liquid may also be conveyed into the open proximal end 370 to provide pressure on the inside of the tube. The gas or liquid can be heated to a temperature sufficient to deform the polymeric tube. This temperature can be above the glass transition temperature of the polymer. The pressure of the gas is selected to sufficiently expand the polymeric tube to conform to the inside surface of cylindrical mold 320. Polymeric tube 300 may be heated by the gas or liquid to a temperature above ambient temperature, for example above Tg of the polymer. Alternatively, heat may be applied to the exterior of cylindrical mold 320. The conveyed gas combined with the applied heat may act to radially expand polymeric tube 300, as indicated by an arrow 380.

Figure 3B:
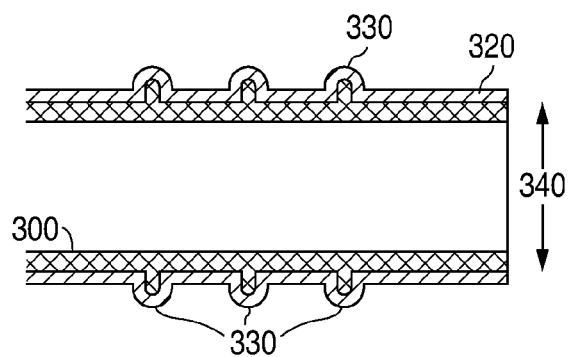
FIG. 3B depicts an axial cross-section of a radially expanded tube after blow molding a gas or liquid into the mold.
Figure 3C:
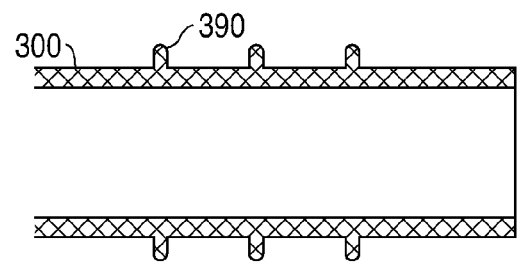
FIG. 3C depicts an axial cross-section of a radially expanded tube having protrusions.
Figure 3D:
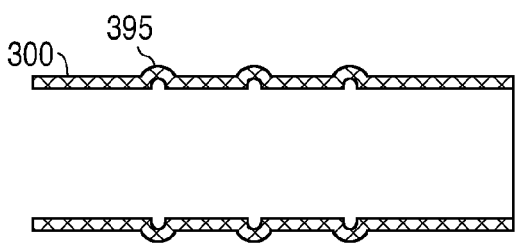
FIG. 3D depicts another embodiment of an axial cross-section of a radially expanded tube having protrusions.

FIG. 3B depicts an axial cross-section of a polymeric tube 300 having protrusions 390 that are formed after blowing a gas at a selected temperature and pressure into the cylindrical mold 320. As depicted in FIG. 3C, tube 300 includes protrusions 390 that are formed during the blow molding process.

Figure 4A:
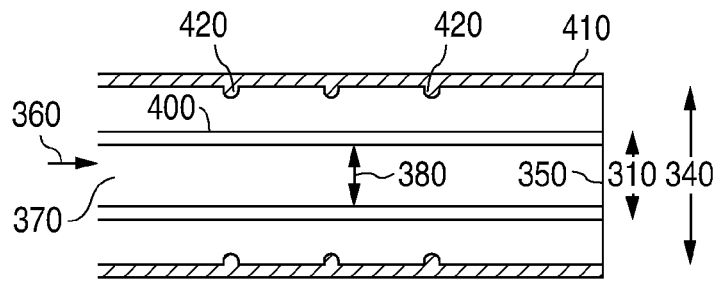
FIG. 4A depicts an axial cross-section of a polymeric tube inserted in a cylindrical mold having protrusions.
Figure 4B:
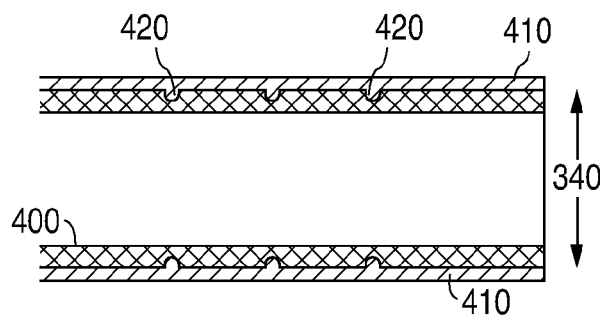
FIG. 4B depicts an axial cross-section of a radially expanded tube after blow molding a gas into the mold.
Figure 4C:
FIG. 4C depicts an axial cross-section of a radially expanded tube having indentations.
Figure 4C:
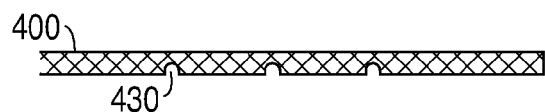
Figure 4D:
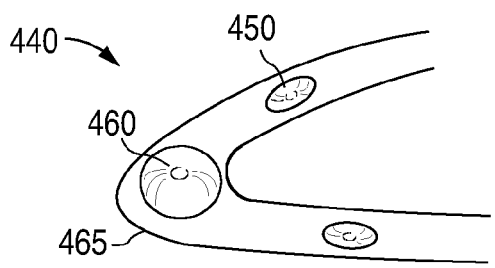
FIG. 4D depicts a stent strut having indentations and a protrusion.

FIG. 4A depicts an axial cross-section of a polymeric tube 400 having an outside diameter 310 positioned within a cylindrical mold 410 having protrusions 420. Cylindrical mold 410 with protrusions 420 acts to limit the expansion of polymeric tube 400 to an expanded diameter 340, which conforms to the surface of the mold. When a polymeric tube 400 expands from diameter 310, indentations 430 are formed in polymeric tube 400. Cylindrical mold 410 includes protrusions 420. FIG. 4B depicts an axial cross-section of a radially expanded tube 400 after blowing a gas or liquid at a selected temperature and pressure into the cylindrical mold 410. As depicted in FIG. 4B, indentations 430 are formed in polymeric tube 400 by blow molding polymeric tube 400 against cylindrical mold 410 having protrusions 420. As depicted in FIG. 4C, tube 400 includes grooves 430 formed during the blow molding process. The indentations in the tube are arranged in the tube as desired. For example, if the indentations are to be used as depots to hold drugs, the indentations may be arranged linearly along the entire length of the tube. Also, the indentations may be arranged such that when the pattern is cut into the tube, the indentations encompass portions of the stent requiring flexibility. The indentations can be of any shape, not just circular. The indentations of the tube are formed to coincide with the specific parts of the stent pattern. For example, FIG. 4D depicts stent strut 440 having indentations 450 and a protrusion 460 on the bending portion 465 of the stent portion. One advantage to forming features on a stent by blow molding rather than by laser cutting is that blow molding avoids deleterious effects on the mechanical portions of the stent caused by heat from lasers that create a heat affected zone.

Figure 5A:
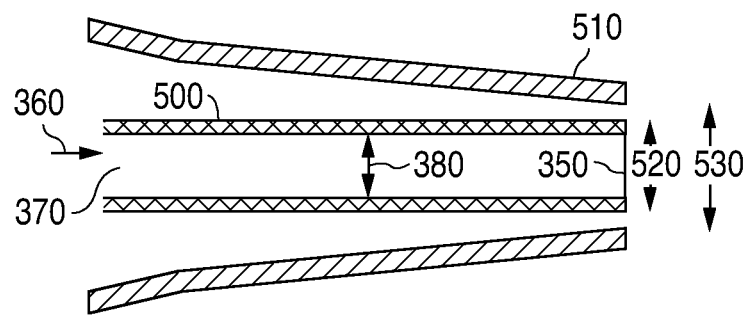
FIG. 5A depicts an axial cross-section of a polymeric tube inserted in a tapered cylindrical mold.
Figure 5B:
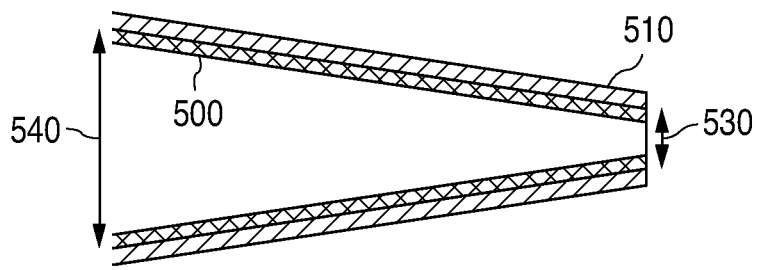
FIG. 5B depicts an axial cross-section of a radially expanded tube after blowing a gas or liquid into the mold.
Figure 5C:
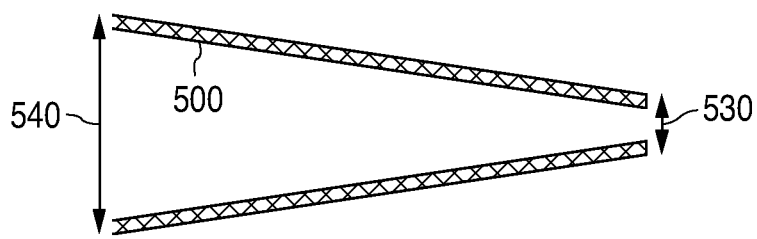
FIG. 5C depicts an axial cross-section of a tapered radially expanded tube.

FIG. 5A depicts an axial cross-section of a polymeric tube 500 with an outside diameter 520 positioned within a cylindrical mold 510, where cylindrical mold 510 is tapered along its length. Cylindrical mold 510 acts to limit the expansion of polymeric tube 500 to an expanded diameter 530 on one end of the polymeric tube 500 and diameter 540 on the other end of the polymeric tube 500. Cylindrical mold 510 has a tapered diameter, such that the diameter 540 on the end of formed tube 500 is expanded more than the other end 530 of tube upon blow molding. FIG. 5B depicts an axial cross-section of a radially expanded tube 500 after blowing a gas at a selected temperature and pressure into the cylindrical mold 510. A tapered polymeric tube 500 is formed by expanding polymeric tube 500 to conform to the inner surface of cylindrical mold 510. As depicted in FIG. 5C, formed tube 500 includes a tapered diameter from diameter 540 to diameter 530. There are many advantages to using a tapered stent. For example, the tapered stent may be adapted to improve the attachment of the stent to the delivery system and facilitate the delivery of the mounted stent into and through a bodily lumen. Although FIGS. 5 depict a uniform tapering shape, the invention includes arbitrary axial cross-sections which can be formed by blow molding.

As mentioned previously, selected portions of the stent using blow molding may be formed to have greater or lesser mass relative to other portions of the stent. For example, high strain regions may be made up of more polymeric mass relative to other portions of the stent. Similarly, lower strain regions that require flexibility may be of a lesser mass.

FIG. 6A depicts a portion of a strut 600 having a uniform thickness on the sidewall 635 and a relatively wider bending portion 620, where width is indicated by "W". That is, thickness 610 of bending portion 620 is substantially the same as the thickness of ends 615 of strut 600. Strut 600 includes a luminal or abluminal side and a side wall 625. The bending portion 620 of strut 600 is bent during crimping the stent onto a balloon-catheter assembly and during expansion of the stent when the stent is deployed. If the abluminal or luminal surface 625 of bending portion 620 is made wider, bending portion 620 of strut 600 is caused to flip upwards or "chip" when the strut is bent 600 during crimping and/or expansion as depicted by arrows 630. Chipping can become problematic because stent protrusion and non-uniform apposition on the vessel wall is unwanted in a vessel wall.

FIGS. 7A and 7B depicts a portion of a strut 700 having a variable thickness. That is, thickness 710 of the bending portion 720 is greater than the thickness of the ends 715 of strut 700. Strut 700 includes a bending portion 720 that is bent during crimping the stent onto a balloon-catheter assembly and/or during expanding the stent when the stent is deployed. As depicted in FIG. 7B, the bending portion 720 of strut 700 may have a low or no tendency to flip outward when the strut is bent during crimping, for example. The greater thickness of the sidewall 735 in bending portion 720 of the stent strut 700 provides a greater strength with little or no out of plane bending as shown in FIG. 6B. In addition, strut portions requiring greater flexibility, such as linking struts, may be formed to be thinner than other strut portions. Therefore, with blow molding, parts having various thicknesses can be designed to be at selected portions of a stent.

In one embodiment, as depicted in FIG. 7C, a portion of a strut 700 has a thicker bending portion 720 as well as protrusions 730 located at selected portions of abluminal or luminal surface 725. In one embodiment, a portion of strut is made to be thicker as well as wider relative to other portions of the stent.

In one embodiment, the polymeric tube may be heated such that the temperature of the polymeric tube is greater than or equal to Tg and less than $T_m$ of the polymer. Heating above Tg facilitates expansion, since a polymer becomes more flexible above Tg.

After the polymeric tube is radially expanded by blow molding the tube, it may be desirable to cool the radially expanded tube below the Tg of the polymer to retain induced molecular orientation. Some embodiments may include cooling the deformed tube prior to fabrication of the medical device. The deformed tube may be cooled at a temperature below an ambient temperature to below the Tg of the polymer. Alternatively, cooling the deformed polymer tube may include cooling the deformed polymer tube at a temperature at or near an ambient temperature to below the Tg of the polymer.

After the polymeric tube is radially expanded by blow molding the tube, the tube may be laser cut to form a stent. A stent may be fabricated by use of a laser beam collimated to a 1 to 10 mm beam diameter. The tube is then cut by focusing a beam, such as a 0.5 to 2 mm wide beam, on the polymeric tube. A stent pattern may then be cut into the tube by moving the tube in an axial and rotary direction with respect to the cutting beam or by moving the beam.

Figure 8:
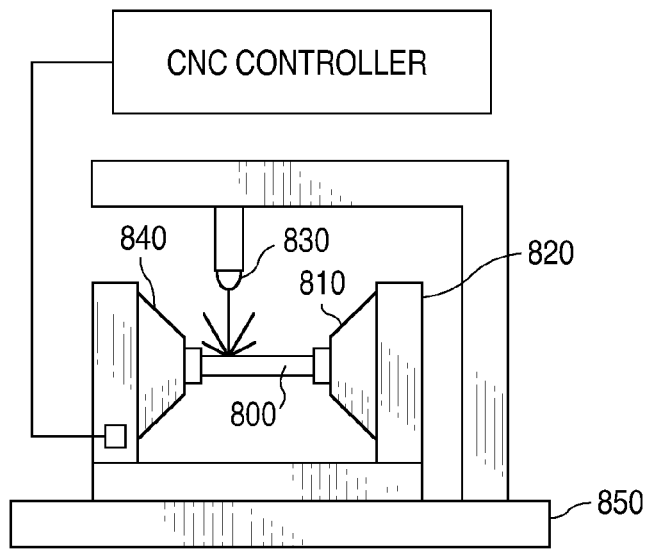
FIG. 8 depicts one embodiment of a machine-controlled system for laser machining a tube, circumventing any features that have been formed on the stent.

FIG. 8 depicts an embodiment of a portion of a machine-controlled system for laser machining a tube. In FIG. 8, a polymeric tube 800 is disposed in a rotatable collet fixture 810 of a machine-controlled apparatus 820 for positioning tube 800 relative to a laser 830. According to machine-encoded instructions, tube 800 is rotated and moved axially relative to laser 830 which may also be machine-controlled. The laser selectively removes the material from the tube resulting in a pattern cut into the tube 800. The tube 800 is therefore cut into the discrete pattern of a finished stent.

The process of cutting a pattern for the stent into the tube is automated except for loading and unloading the length of tube 800. Referring again to FIG. 8, the process may be done, for example, using a CNC-opposing collet fixture 840 for axial rotation of the length of tubing. Collet fixture 840 may act in conjunction with a CNC X/Y table 850 to move the length of tube axially relative to a machine-controlled laser 830 as described. The entire space between collets can be patterned using a laser set-up of the foregoing example. The program for control of the apparatus is dependent on the particular configuration used and the pattern formed. Therefore, a pattern that circumvents any features formed on the tube can be accomplished using the program for control of the apparatus.

Machining a fine structure also requires the ability to manipulate the tube with precision. CNC equipment manufactured and sold by Anorad Corporation in Hauppauge, N.Y. may be used for positioning the tube. In addition, a unique rotary mechanism may be used that allows the computer program to be written as if the pattern were being machined from a flat sheet, allowing utilization of both circular and linear interpolation in programming. Thus, the axial and rotary motion may be controlled by a CNC system. A CNC controlled axis may also control the focus position on the polymeric tube. After indexing the CNC system to a specific position on tube, the system traces the pattern in the x, y, z coordinate system. Since the finished structure of the stent is very small, a precision drive mechanism is required that supports and drives both ends of the tubular structure as it is cut. Since both ends are driven, they are preferably aligned and precisely synchronized. Otherwise, as the stent is being cut, the stent may twist and distort.

The stent produces stents with a fine precision structure cut from a small diameter thin-walled cylindrical tube. Cutting a fine structure around features on a stent surface created by the present invention (e.g., a 0.0035 inch strut width (0.889 mm)) requires precise laser focusing and minimal heat input. To satisfy these requirements, a laser technology adapted to micro-machine the tube may be implemented according to the present embodiments.

Figure 9B:
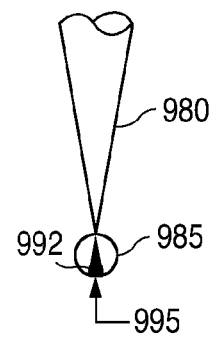
FIG. 9(b) depicts a close-up end view of a region where a laser beam interacts with a tube having features.
Figure 9A:
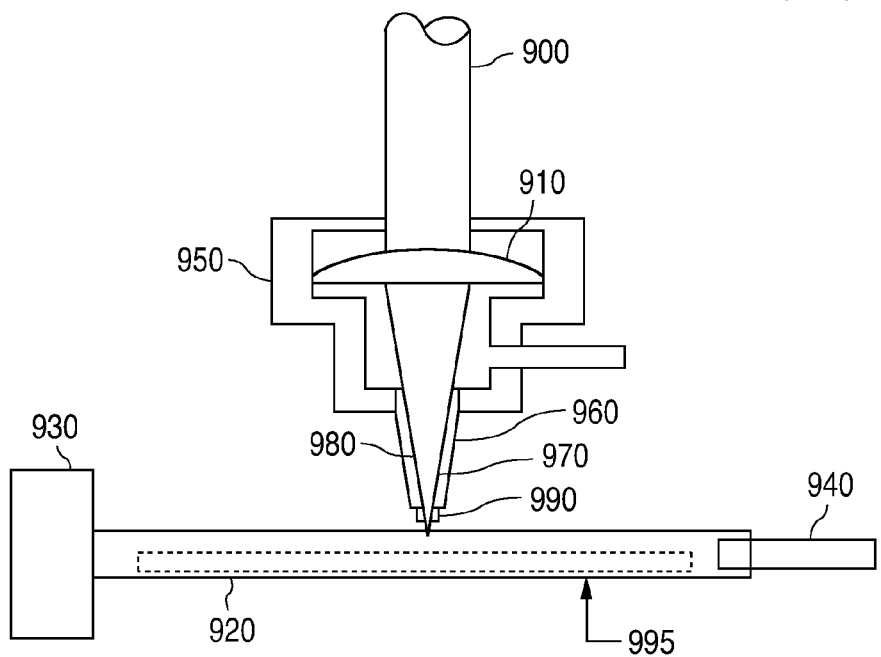
FIG. 9(a) depicts a close-up axial view of a region where a laser beam interacts with a tube having features.

Additionally, FIGS. 9(a) and 9(b) show that apparatus 900 incorporates a monocular viewing, focusing, and cutting head 930. A rotary axis 940 and X-Y stages 950 for rotating and translating the work piece are also shown. A CNC controller 960 is also incorporated into apparatus 300.

FIG. 9(a) depicts a close-up axial view of the region where the laser beam interacts with the substrate target material. A laser beam 900 is focused by a focusing lens 910 on a tube 920 is supported by a CNC controlled rotary collet 930 at one end and a tube support pin 940 at another end.

As shown by FIG. 9(a), the laser can incorporate a coaxial gas jet assembly 950 having a coaxial gas jet 960 and a nozzle 970 that helps to remove debris from the kerf and cools the region where the beam interacts with the material as the beam cuts and vaporizes a substrate. Coaxial gas jet nozzle 970 (e.g., 0.018 inch diameter (0.457 mm)) is centered around a focused beam 980 with approximately 0.010 inch (2.54 mm) between a tip 990 of nozzle 970 and a tube 920. In certain embodiments, an optical system for modifying a laser beam according to the embodiments described herein may be positioned between cutting head 930 (depicted in FIGS. 9(a) and 9(b)) and the substrate target material.

It may also be necessary to block laser beam 980 as it cuts through the top surface of the tube to prevent the beam, along with the molten material and debris from the cut, from impinging on the inside opposite surface of tube 990. To this end, a mandrel 992 (e.g., approx. 0.034 inch diameter (0.864 mm)) supported by a mandrel beam block 995 is placed inside the tube and is allowed to roll on the bottom of the tube 985 as the pattern is cut, which acts as a beam/debris block protecting the far wall inner diameter. A close-up end view along mandrel beam block 995 shows laser beam 980 impinging on tube 985 in FIG. 9(b).

Hence, the laser enables the machining of narrow kerf widths to circumvent the features formed on the stent surface, while minimizing the heat input into the material. In this way, smooth, narrow cuts in a tube with very fine geometries are made without damaging the narrow struts that define the stent structure.

The stent can be made partially or completely from a biodegradable, bioabsorbable, or biostable polymer. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. For stents made from a biodegradable polymer, the stent is intended to remain in the body for a duration of time until its intended function is accomplished.

Representative examples of polymers that may be used to fabricate a stent using the methods disclosed herein include poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(D,L-lactic acid), poly(glycolic acid-co-trimethylene carbonate), poly(trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating a stent according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), poly(L-lactic acid), poly(caprolactone), ethylene-vinyl acetate copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a stent, the method comprising:
   disposing a polymeric tube into a cylindrical mold, the cylindrical mold comprising an inner surface facing the polymeric tube, the inner surface having an inner diameter that varies along an axial length of the cylindrical mold;
   expanding the polymeric tube in radially outward directions to form an expanded tube, the expanding including blowing a gas or liquid into the cylindrical mold so that an outer surface of the polymeric tube conforms to the inner surface of the cylindrical mold and so that the outer surface of the expanded tube has an outer diameter that varies along an axial length of the expanded tube; and followed by
   cutting the expanded tube to form interconnecting struts.

2. The method of claim 1, wherein the outer surface of the expanded tube is tapered such that the outer diameter increases from an end segment of the expanded tube to an opposite end segment of the expanded tube.

3. The method of claim 2, wherein the outer diameter increases continuously from the end segment to the opposite end segment.

4. The method of claim 1, wherein the outer surface forms a conical shape.

5. The method of claim 1, wherein the expanded tube comprises a first end segment, a second end segment opposite the first end segment, and a central segment between the first and second end segments, and wherein the outer surface of the expanded tube is tapered such that the outer diameter is greater at the first end segment than at the central segment and is greater at the central segment than at the second end segment.

6. The method of claim 1, wherein the expanded tube comprises a first end segment, a second end segment opposite the first end segment, and a central segment between the first and second end segments, and wherein the outer diameter is larger at the central segment than at the first and second end segments.

7. The method of claim 1, wherein the expanded tube comprises a first end segment, a second end segment opposite the first end segment, and a central segment between the first and second end segments, and wherein the outer surface of the expanded tube is tapered such that the outer diameter increases from the first end segment to the central segment.

8. The method of claim 7, wherein the outer diameter increases from the second end segment to the central segment.

9. The method of claim 1, further comprising heating the polymeric tube to a temperature above Tg of the polymer either before or during the expanding.

10. The method of claim 1, further comprising heating the polymeric tube to a temperature above Tg of the polymer before and during the expanding.

11. The method of claim 10, wherein the polymeric tube is heated by the liquid or gas blown into the cylindrical mold.

12. The method of claim 1, wherein the interconnecting struts are configured to be crimped and expanded.

13. The method of claim 1, wherein the polymeric tube comprises a biodegradable and/or biostable polymer.

14. The method of claim 1, wherein the polymeric tube is made of poly(L-lactic acid).

15. The method of claim 1, wherein the polymeric tube is made of poly(lactide-co-glycolide).

16. The method of claim 1, wherein the expanding creates an induced molecular orientation with the polymeric tube, and wherein each strut, prior to crimping, has the induced molecular orientation which is the same as in an adjacent one of the struts.

17. The stent of claim 16, wherein the outer surface of the polymeric tube, after expanding, has a shape corresponding to the inner surface of the cylindrical mold.

18. The method of claim 1, wherein the cutting is performed while no delivery system is disposed within the stent.

* * * * *